United States Patent
Sato et al.

(10) Patent No.: US 11,906,346 B2
(45) Date of Patent: Feb. 20, 2024

(54) LIQUID LEVEL DETECTION DEVICE THAT IRRADIATES A CONTAINER AT MULTIPLE ANGLES

(71) Applicant: HITACHI HIGH-TECH CORPORATION, Tokyo (JP)

(72) Inventors: Fumiyasu Sato, Tokyo (JP); Masahito Kakuno, Tokyo (JP); Nobuyoshi Shimane, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 498 days.

(21) Appl. No.: 17/268,705

(22) PCT Filed: Aug. 22, 2019

(86) PCT No.: PCT/JP2019/032744
§ 371 (c)(1),
(2) Date: Feb. 16, 2021

(87) PCT Pub. No.: WO2020/040239
PCT Pub. Date: Feb. 27, 2020

(65) Prior Publication Data
US 2021/0231483 A1    Jul. 29, 2021

(30) Foreign Application Priority Data
Aug. 23, 2018  (JP) .................................. 2018-155954

(51) Int. Cl.
*G01F 23/292*    (2006.01)
*G01N 35/10*     (2006.01)

(52) U.S. Cl.
CPC ....... *G01F 23/292* (2013.01); *G01N 35/1009* (2013.01); *G01N 2035/1025* (2013.01)

(58) Field of Classification Search
CPC .............. G01F 23/292; G01N 35/1009; G01N 2035/1025
See application file for complete search history.

(56) References Cited

U.S. PATENT DOCUMENTS 9,470,674 B2   10/2016   Klinec
9,534,885 B2    1/2017   Klinec et al.
(Continued)

FOREIGN PATENT DOCUMENTS

JP   2012-173226 A   9/2012
JP      5993388 B2   9/2016

OTHER PUBLICATIONS

Extended European Search Report received in corresponding European Application No. 19852724.4 dated Mar. 25, 2022.
(Continued)

*Primary Examiner* — Eric S. McCall
(74) *Attorney, Agent, or Firm* — MATTINGLY & MALUR, PC

(57) ABSTRACT

A liquid level detection device capable of accurately detecting an interface inside a container has an irradiation unit which irradiates a side surface of a sample container containing a sample having layers with light. A light receiving unit receives transmitted light from the sample container and an analysis unit acquires the interfaces between the layers from the received amount of the transmitted light. The sample container is moved vertically relative to the irradiation unit and the light receiving unit by a first drive and is moved in the circumferential direction relative to the irradiation unit and the light receiving unit by a second drive. The second drive is controlled so that the light receiving unit receives the transmitted light at first and second irradiation angles, and the interfaces between the layers are acquired on (Continued)

the basis of the received amounts of transmitted light at the first and second irradiation angles.

8 Claims, 13 Drawing Sheets

(56) References Cited

U.S. PATENT DOCUMENTS

2004/0260520 A1  12/2004  Braendle et al.
2016/0018427 A1   1/2016  Streibl et al.

OTHER PUBLICATIONS

International Search Report of PCT/JP2019/032744 dated Sep. 17, 2019.

[FIG. 1]
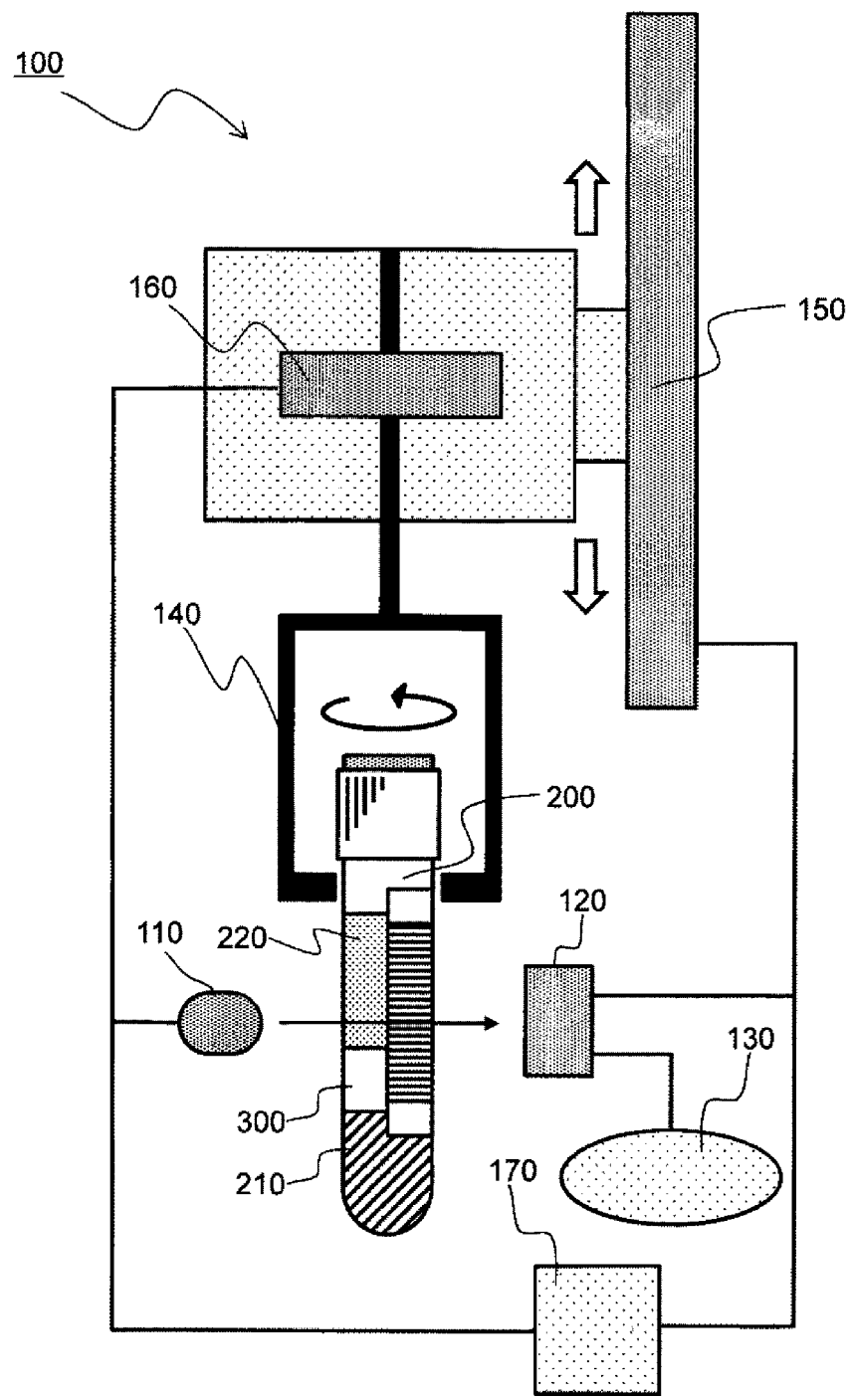

[FIG. 2A]
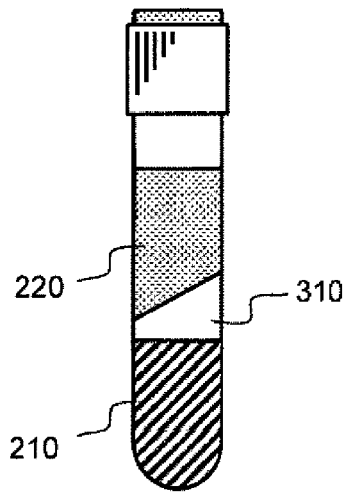
[FIG. 2B]
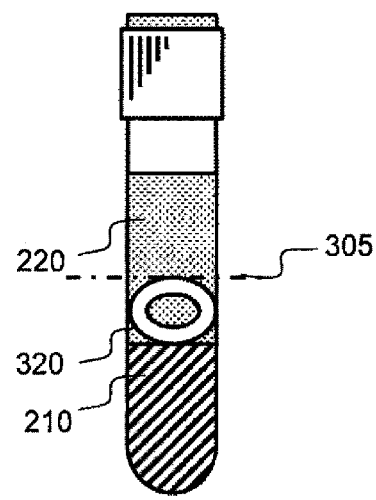

[FIG. 2C]
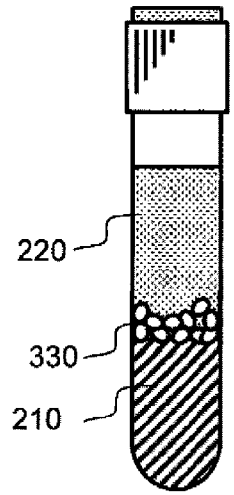
[FIG. 2D]
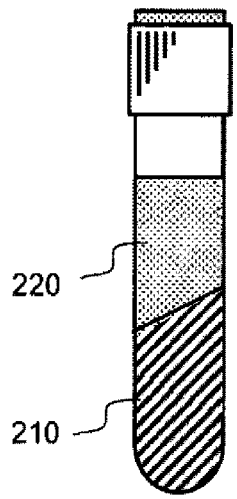

[FIG. 3]
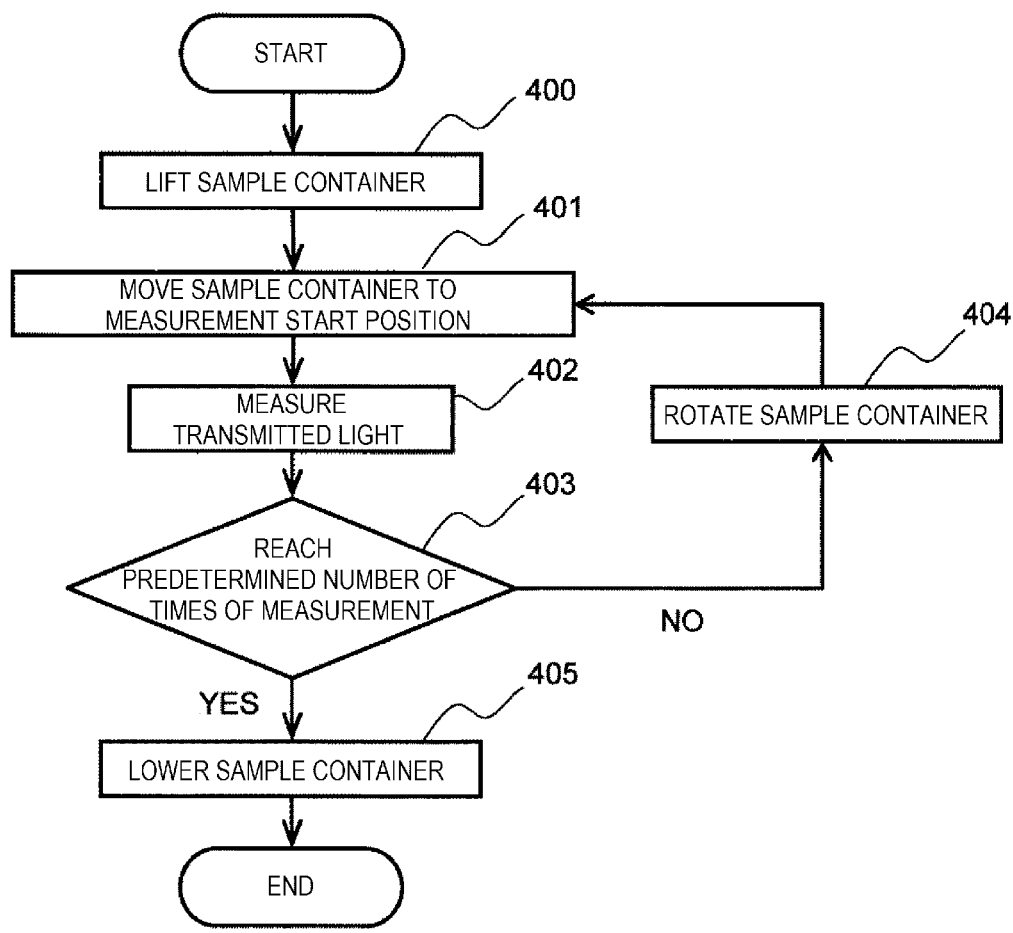

[FIG. 4A]
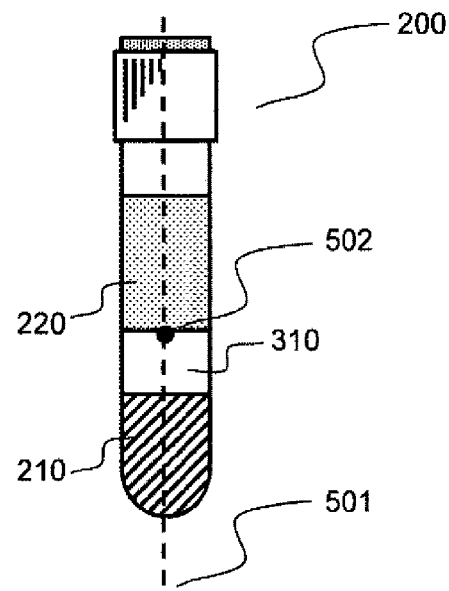
[FIG. 4B]
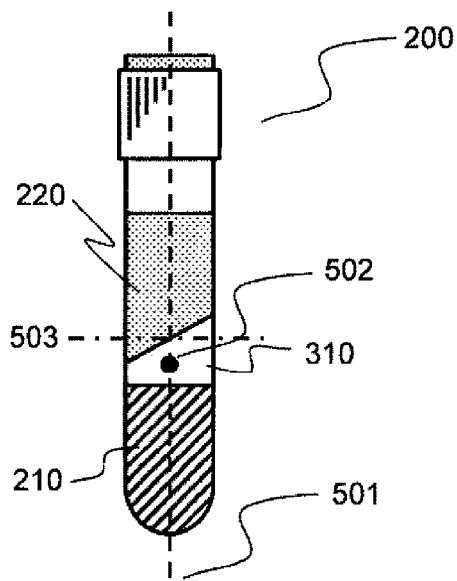

[FIG. 4C]
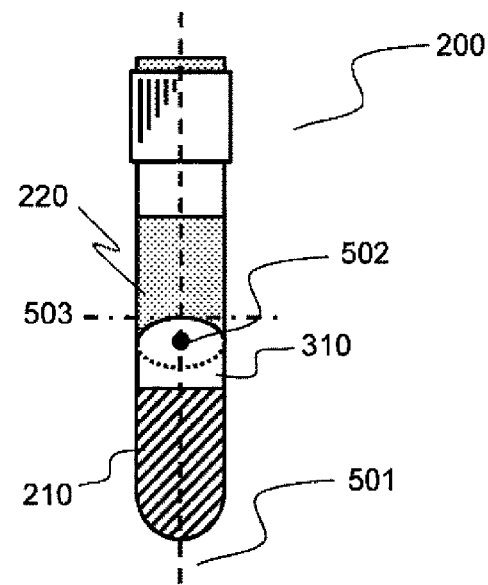
[FIG. 5]
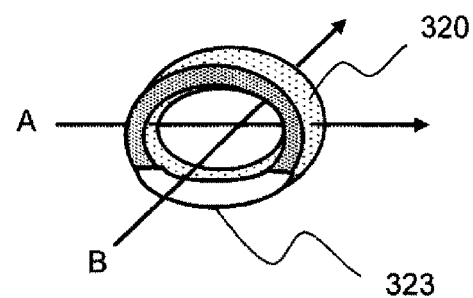

[FIG. 6]
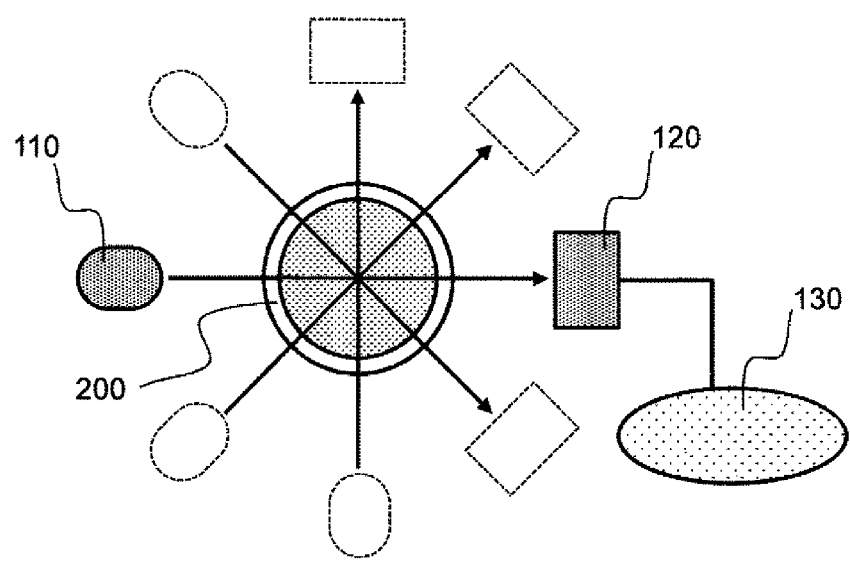

[FIG. 7]
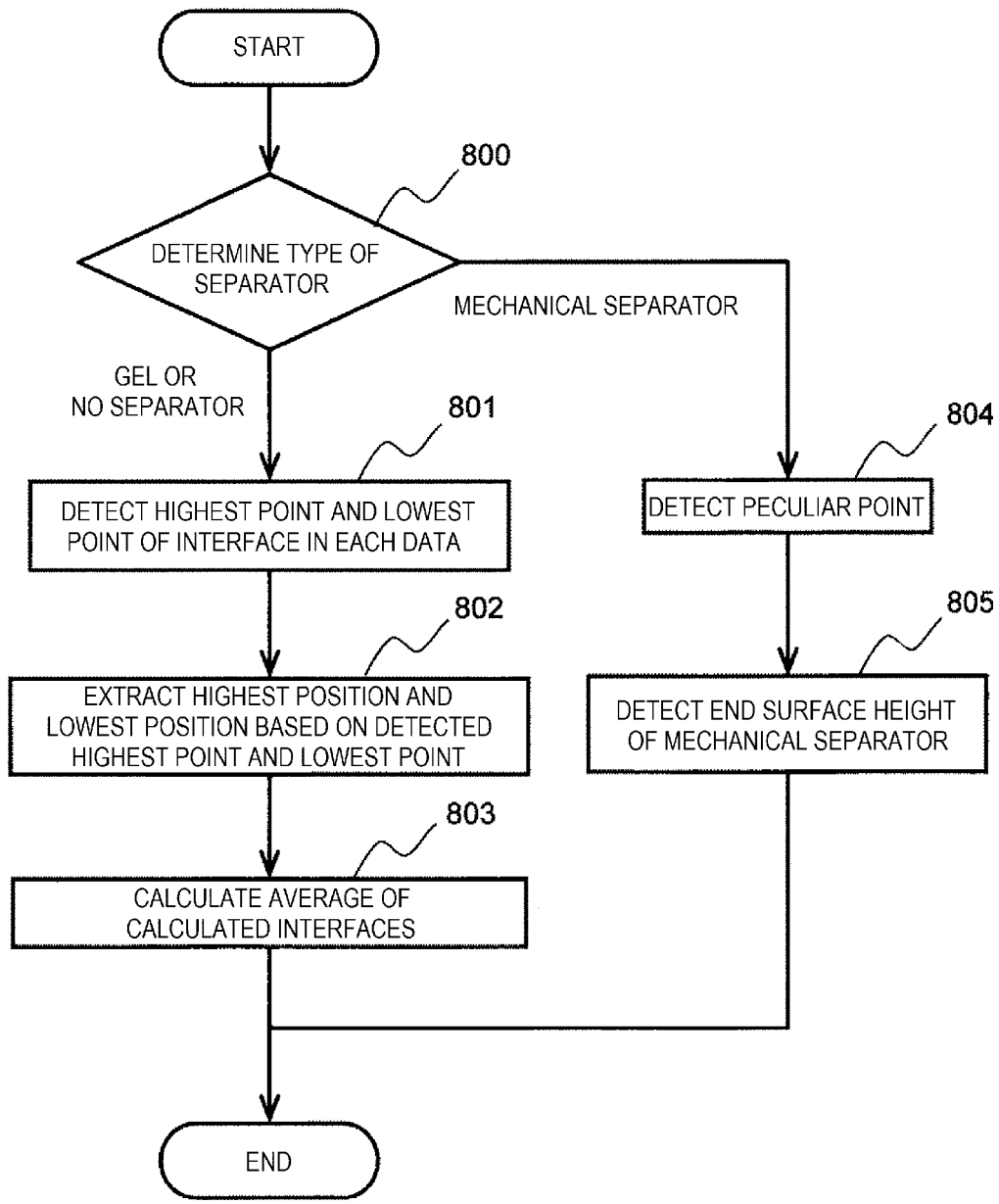

[FIG. 8A]
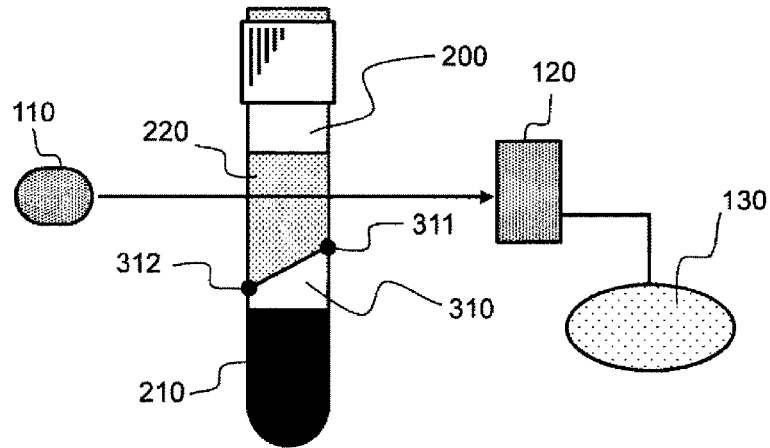
[FIG. 8B]
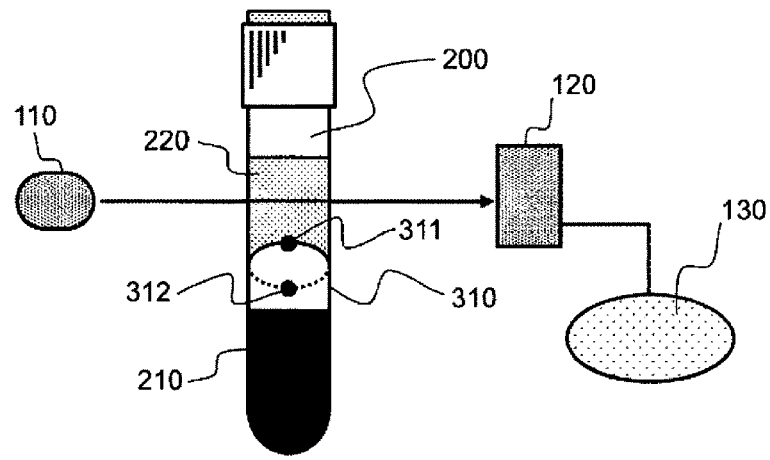
[FIG. 8C]
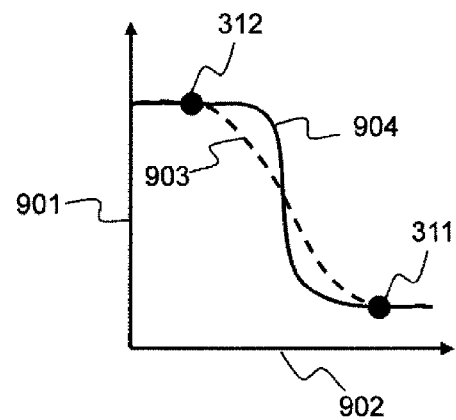

[FIG. 9A]
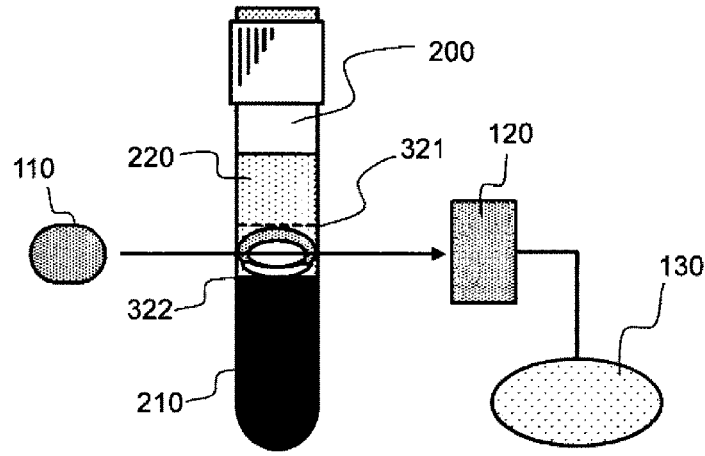
[FIG. 9B]
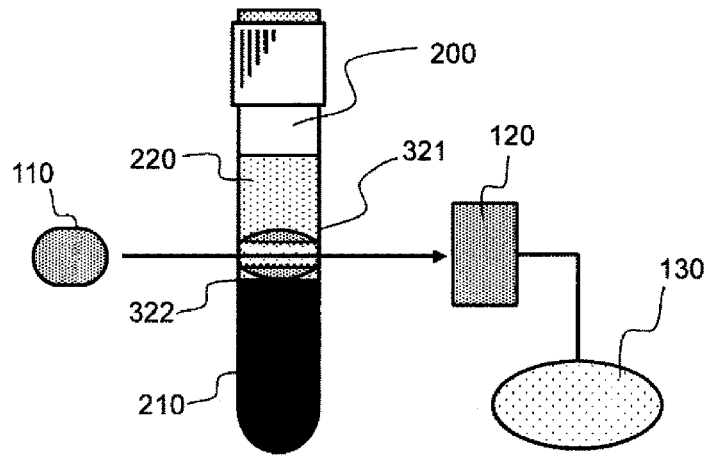
[FIG. 9C]
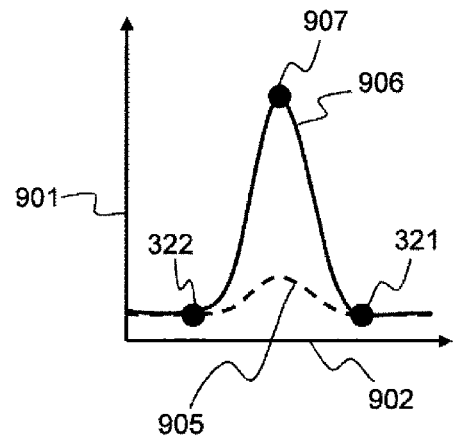

[FIG. 10]
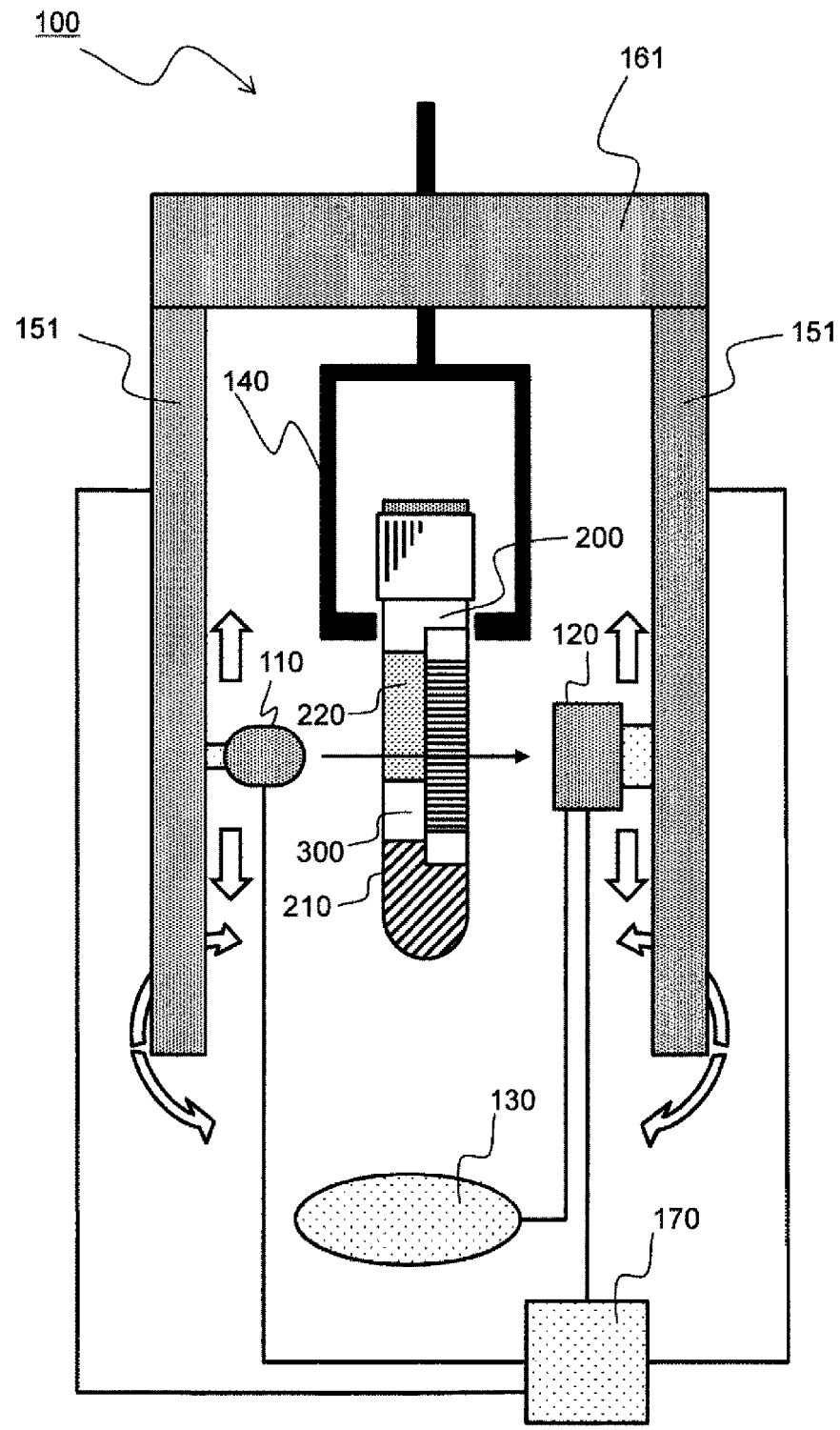

[FIG. 11]
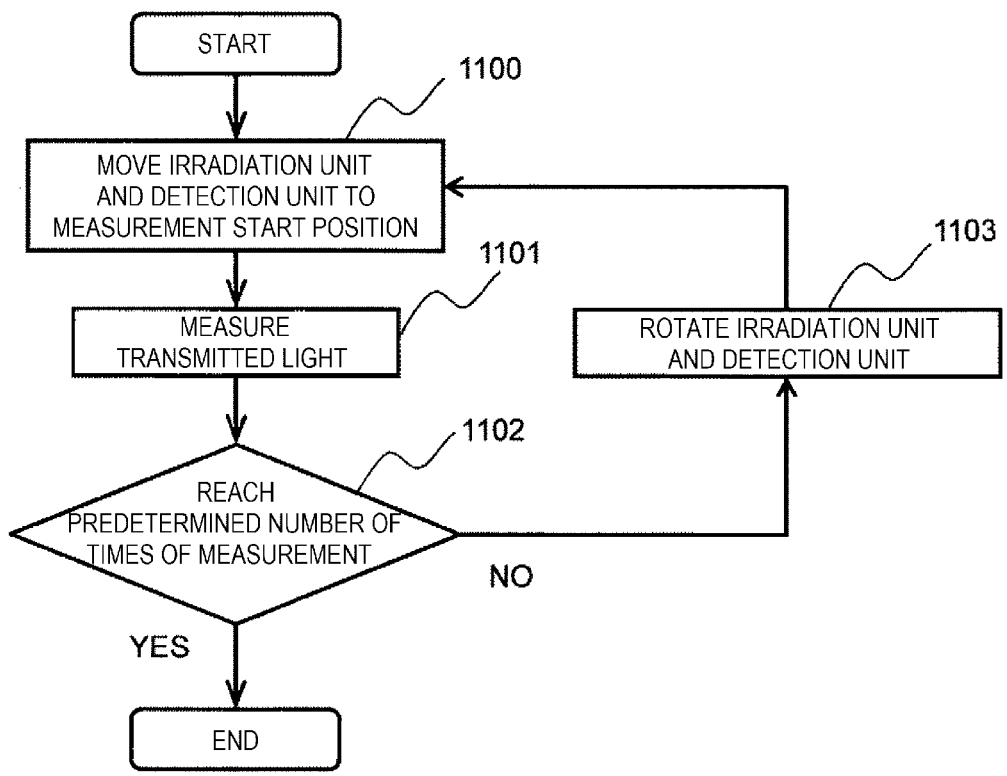

[FIG. 12]
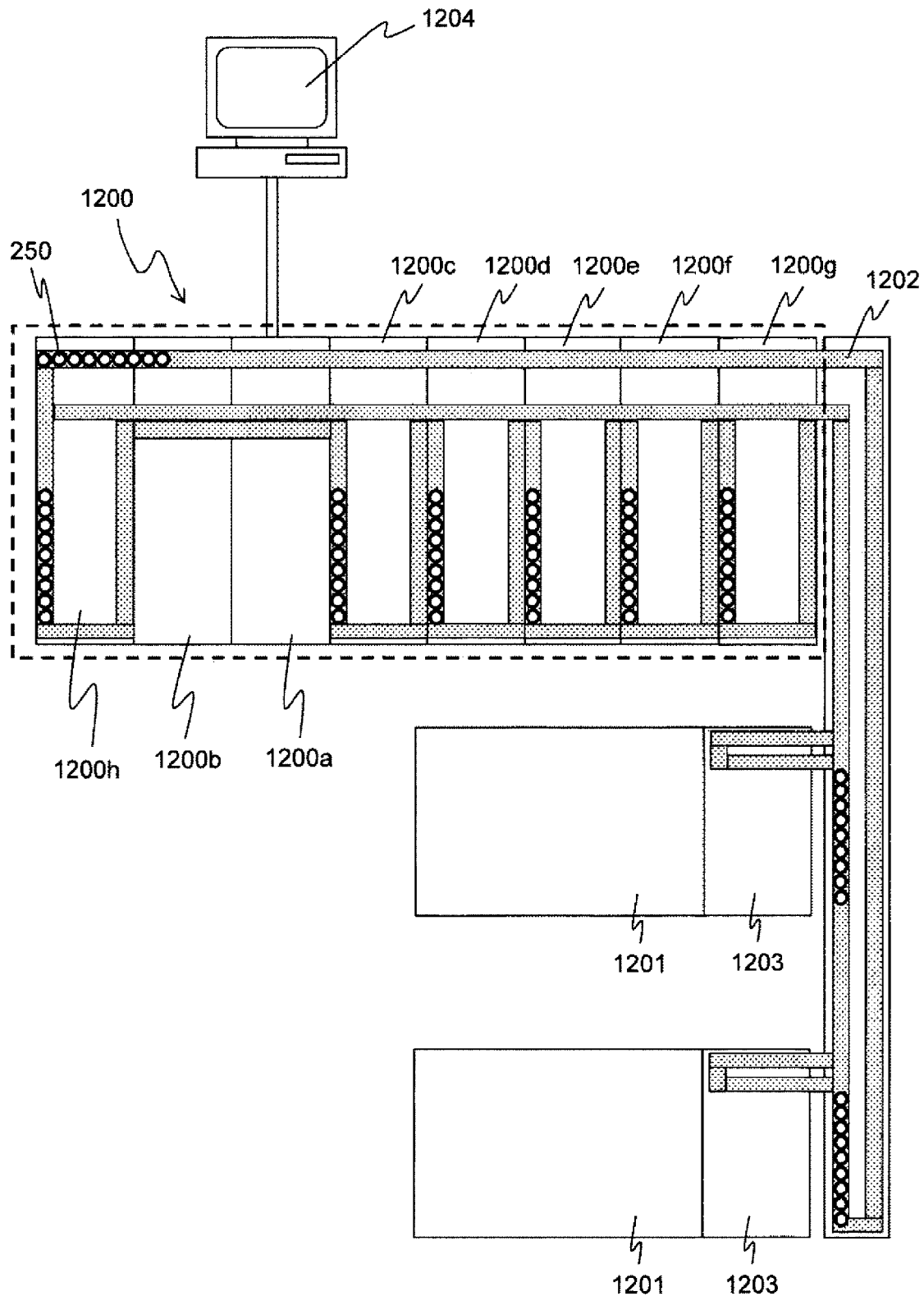

LIQUID LEVEL DETECTION DEVICE THAT IRRADIATES A CONTAINER AT MULTIPLE ANGLES

TECHNICAL FIELD

The present invention relates to a liquid level detection device.

BACKGROUND ART

An automatic analysis device that performs qualitative and quantitative analysis on samples such as blood and urine is used. A sample inspection automation system that automatically performs pretreatment processing such as centrifugation on a sample and transport processing such as transporting a sample to an automatic analysis device is also used.

In the pretreatment processing, the centrifugation of the sample and detection of a liquid level of the sample after the centrifugation may be performed. For example, when the sample is blood, the blood is separated into serum (or plasma) and clot by the centrifugation. The sample container that contains the sample may be provided with a separator to separate the serum (or plasma) and the clot, and the serum, the separator, and the clot are contained in layers in the sample container after the centrifugation. After this centrifugation, a liquid level detection device of the sample inspection automation system measures an interface of the layers in the sample container and a liquid volume.

PTL 1 discloses a liquid level detection device that detects a liquid level existing in a sample container by controlling a relative position between an irradiation unit and a detection unit such that the detection unit is moved to a position where transmitted light can be detected in conjunction with moving the irradiation unit that irradiates a part of the sample container containing a liquid substance with light in a direction parallel to an axis of the sample container, and detecting the transmitted light for an entire length of the sample container.

CITATION LIST

Patent Literature

PTL 1: JP-A-2012-173226

SUMMARY OF INVENTION

Technical Problem

PTL 1 does not examine a case where a separator other than a gel is used or a case where the liquid level is not flat.

Therefore, an object of the invention is to provide a liquid level detection device capable of accurately detecting an interface inside a container regardless of a type of a separator or a state of the interface.

Solution to Problem

In order to solve the problems, for example, a configuration described in claims is adopted.

The invention includes a plurality of manners for solving the problems, and an example thereof is a liquid level detection device including: an irradiation unit configured to irradiate a side surface of a sample container containing a sample having layers with light; a light receiving unit configured to receive transmitted light that is the light emitted from the irradiation unit and passing through the sample container; an analysis unit configured to acquire an interface between the layers of the sample contained in the sample container based on received amounts of the transmitted light received by the light receiving unit; a first drive unit configured to move the sample container in a vertical direction relative to the irradiation unit and the light receiving unit; a second drive unit configured to move the sample container in a circumferential direction of the sample container relative to the irradiation unit and the light receiving unit; and a control unit configured to control the first drive unit and the second drive unit, in which the control unit controls the second drive unit, so that the irradiation unit irradiates the sample container with the light at a first irradiation angle and a second irradiation angle different from the first irradiation angle, and the light receiving unit receives transmitted light that is the light passing through the sample container, and the analysis unit acquires an interface between the layers of the sample based on received amounts of transmitted light at the first irradiation angle and the second irradiation angle.

Advantageous Effect

According to the invention, a liquid level detection device capable of accurately detecting an interface inside a container regardless of a type of a separator or a state of the interface can be provided.

Problems, configurations and effects other than those described above will become apparent from the following description of the embodiments.

BRIEF DESCRIPTION OF DRAWINGS

FIG. 1 is an overall configuration diagram of a liquid level detection device according to a first embodiment.

FIG. 2A is a side view of a sample container after being subjected to centrifugation using a gel.

FIG. 2B is a side view of a sample container after being subjected to centrifugation using a mechanical separator.

FIG. 2C is a side view of a sample container after being subjected to centrifugation using beads.

FIG. 2D is a side view of a sample container after being subjected to centrifugation without using a separator.

FIG. 3 is a flowchart showing a flow of measurement operations of transmitted light according to the first embodiment.

FIG. 4A is a diagram showing an irradiation path and an irradiation position of light to a sample container (interface being horizontal).

FIG. 4B is a diagram showing an irradiation path and an irradiation position of light to a sample container (interface being inclined).

FIG. 4C is a diagram showing an irradiation path and an irradiation position of light at a position where the sample container of FIG. 4B is rotated 90 degrees clockwise when viewed from above.

FIG. 5 is a diagram showing a shape of a mechanical separator.

FIG. 6 is a top view showing a state of measuring transmitted light from a plurality of directions.

FIG. 7 is a flowchart showing a flow for acquiring an interface according to the first embodiment.

FIG. 8A is a diagram showing a state of measuring a sample container in which a gel is used.

FIG. 8B is a diagram showing a state of measurement in which the sample container of FIG. 8A is rotated 90 degrees clockwise when viewed from above.

FIG. 8C is a diagram showing data on an amount of transmitted light near an upper end surface of the gel.

FIG. 9A is a diagram showing a state of measuring a sample container in which a mechanical separator is used.

FIG. 9B is a diagram showing a state of measurement in which the sample container of FIG. 9A is rotated 90 degrees clockwise when viewed from above.

FIG. 9C is a diagram showing data on an amount of transmitted light near an upper end surface of the mechanical separator.

FIG. 10 is an overall configuration diagram of a liquid level detection device according to a second embodiment.

FIG. 11 is a flowchart showing a flow of measurement operations of transmitted light according to the second embodiment.

FIG. 12 is an overall configuration diagram of a sample inspection automation system.

DESCRIPTION OF EMBODIMENTS

Hereinafter, embodiments of the invention will be described with reference to the drawings.

First Embodiment

FIG. 1 is an overall configuration diagram of a liquid level detection device 100 according to the present embodiment.

The liquid level detection device 100 is mainly configured with an irradiation unit 110, a light receiving unit 120, an analysis unit 130, a gripping portion 140, a first drive unit 150, a second drive unit 160, and a control unit 170.

A sample container 200 contains a sample. The sample container 200 is a substantially transparent bottomed cylinder container made of various resin materials, various glass materials, and the like, which is elongated vertically, and is a cylindrical or tapered container. There are various types of sample containers 200, and users use the various types of sample containers 200 properly according to respective uses thereof. The various types of sample containers 200 have various shapes, different diameters, different heights, different stoppers, and the like, and are mixed and used. In the present embodiment, a test tube is used as the sample container 200.

The sample contained in the sample container 200 is separated into a layer of a substance having a relatively high specific gravity and a layer of a substance having a relatively low specific gravity by centrifugation. The sample container 200 may contain a separator 300 having an intermediate specific gravity between these substances. In the present embodiment, a blood sample collected from a patient is used as the sample. The blood sample is separated into a clot 210 having a relatively high specific gravity and a serum 220 (or plasma) having a relatively low specific gravity by centrifugation. The separator 300 is contained in the sample container 200, and after the centrifugation, the clot 210 and the serum 220 are separated by the separator 300.

In addition to the blood sample, the sample may be a biological sample such as urine, a mixed solution of a biological sample and a reagent, or a reaction solution obtained by the biological sample reacting with the reagent, or the like.

The irradiation unit 110 irradiates a side surface of the sample container 200 with light.

The light receiving unit 120 receives transmitted light that is light emitted from the irradiation unit 110 and passing through the sample container 200.

The gripping portion 140 grips the sample container 200. The gripping portion 140 is driven by the first drive unit 150 and the second drive unit. The first drive unit 150 moves the sample container 200 vertically, and the second drive unit 160 rotates the sample container 200 around a vertical direction of the sample container 200 as a rotation axis (that is, in a circumferential direction of the sample container 200).

The analysis unit 130 acquires an interface between liquids (layers) in the sample container, an interface between a liquid and a gas, or an interface between the separator and the liquid based on data of the transmitted light acquired by the light receiving unit 120.

The control unit 170 controls operations of the irradiation unit 110, the light receiving unit 120, the first drive unit 150, and the second drive unit 160.

The control unit 170 may have functions of the analysis unit 130. Further, the functions of the control unit 130 and the control unit 170 may be provided by a control device provided outside the liquid level detection device 100.

FIG. 2A to FIG. 2D show side views of the sample container 200 after being subjected to the centrifugation.

FIG. 2A shows a case in which a gel 310 is used as the separator 300, FIG. 2B shows a case in which a mechanical separator 320 is used as the separator 300, and FIG. 2C shows a case in which beads 330 are used as the separator. Depending on an analysis item, the separator may not be used as shown in FIG. 2D.

FIG. 3 is a flowchart showing a flow of liquid level detection in the present embodiment. When the sample container 200 arrives at the liquid level detection device 100, the control unit 170 starts detection operations and performs processing as follows.

The gripping portion 140 driven by the first drive unit 150 grips and lifts the sample container 200 that arrives at the liquid level detection device 100 (step 400).

The sample container 200 is moved by the first drive unit 150 to a liquid level measurement start position (step 401). The measurement start position may be at an upper side or a lower side of the test tube.

The irradiation unit 110 irradiates the sample container 200, which is moved vertically from the measurement start position by the first drive unit 150, with the light, the light receiving unit 120 receives the transmitted light passing through the sample container 200, and the transmitted light is measured (step 402). At this time, while the sample container is moved vertically, the data of the transmitted light for an entire length of the sample container 200 is acquired.

Since a light transmittance differs depending on a type of the liquid and the separator, when a light irradiation position is the interface between the liquid and the separator, the interface between different liquids, or the interface between the liquid and the gas, a received amount of the transmitted light (which may be considered to be brightness) changes significantly. Therefore, it is possible to determine a position where the received amount of the transmitted light is significantly changed as the interface. In other words, in step 402, the sample container 200 is scanned vertically at a first position (irradiation angle) in the circumferential direction, and data indicating the change in the amount of transmitted light is acquired.

The movement of the irradiation position (or the acquisition of the data of the transmitted light) in step 402 may be performed for the entire length of the sample container, or may be performed within a necessary range when an approximate position of the interface or the like is known.

The measurement of the transmitted light in step 402 is performed a predetermined number of times. Therefore, after the transmitted light is measured in step 402, it is determined whether or not the measurement in step 402 is performed the predetermined number of times (step 403). The number of times of the measurement in step 402 may always be a fixed number, or the number of times of the measurement may be set for each sample container 200 and the type of the sample.

When the predetermined number of times is not reached, the second drive unit 160 rotates the sample container 200 to change the light irradiation position (step 404). At this time, the sample container is rotated, so that the light irradiation positions on the sample container do not overlap. Then, the processing returns to step 401, the container is moved to the measurement start position, and the transmitted light for the entire length of the sample container in step 402 is measured again. In other words, in step 402 performed after step 404, the sample container 200 is scanned vertically from a position (a second, a third, . . . , an Nth position (irradiation angle), and N indicates the above-mentioned predetermined number of times) in the circumferential direction different from the first position, and data indicating the change in the amount of transmitted light is acquired.

In step 404, after the sample container 200 is rotated, the sample container 200 is moved to the measurement start position, and the sample container 200 may be moved to the measurement start position and then the sample container 200 may be rotated, or the sample container 200 may be moved to the measurement start position and be rotated at the same time. Further, a measurement end position may be set as the measurement start position, and the sample container 200 may be rotated to start next measurement.

When it is determined in step 403 that the predetermined number of times of measurement is reached, the sample container 200 is returned to a position before being lifted by the first drive unit 150, and the gripping portion 140 stops gripping the sample container 200 (step 405). After this, the sample container 200 is transported to a next process.

FIG. 4A to FIG. 4C show examples of the irradiation positions of the light from the irradiation unit 110 to the sample container 200. A dotted line indicates an irradiation path 501 of the light, and a black circle on the irradiation path 501 indicates an irradiation position 502 of the light. In FIG. 4A to FIG. 4C, the irradiation unit 110 irradiates the sample container 200 with the light in a depth direction of the drawing.

The irradiation position 502 moves the entire length of the sample container 200 along the irradiation path 501. In the present embodiment, the movement of the irradiation position 502 is implemented by the first drive unit 150 vertically moving the sample container 200.

In step 402 of FIG. 3, the interface is acquired based on the data of the transmitted light acquired at the light irradiation position for the entire length of the sample container. When the interface is horizontal as shown in FIG. 4A, a same height can be detected as the interface regardless of a direction of light irradiation.

However, when the interface is not horizontal, a position detected as the interface differs depending on the irradiation position 502 of the light.

FIG. 4B shows a case where the interface is inclined. FIG. 4C is a diagram showing the irradiation path 501 and the irradiation position 502 of the light when the sample container of FIG. 4B is measured at a position rotated 90 degrees clockwise when viewed from above. Since an intersection of the irradiation path 501 of the light and the interface is detected as the interface, in FIG. 4B, a position of a dotted line 503 is detected as the interface between the serum 220 and the gel 310. On the other hand, in FIG. 4C, a position of the dotted line 503 at an uppermost portion of the interface between the serum 220 and the gel 310 is detected as the interface.

In FIG. 4B, since the gel 310 is located above the position detected as the interface (dotted line 503), when a probe is lowered with reference to the dotted line 503, during dispensing, the gel 310 may be sucked and a clogging error may occur. On the other hand, in FIG. 4C, since the position detected as the interface (dotted line 503) is the uppermost portion of the interface between the gel 310 and the serum 220, when the probe is lowered with reference to the dotted line 503, the serum 220 can be sucked without contaminating the probe. However, in a case where a serum amount is to be acquired, when the uppermost portion of the interface between the gel 310 and the serum 220 is set as the interface, the serum amount is estimated to be lower than an actual serum amount. Further, when a lowermost portion of the interface between the gel 310 and the serum 220 is estimated as the interface, the serum amount is estimated to be larger than the actual amount.

The case where the separator 300 is the gel 310 is described, but the interface may not be horizontal even when a separator such as the beads 330 other than gel 310 or the separator is not used.

Further, the mechanical separator 320 has a light irradiation direction through which the interface is easily detected. A case where a position of a dotted line 305 in FIG. 2B is detected as an interface between the mechanical separator 320 and the serum 220 is considered as an example. FIG. 5 shows a shape of the mechanical separator 320. The mechanical separator has a structure in which a lower portion 323 is on a lower side after being subjected to the centrifugation. Arrows A, B indicate irradiation directions of the light emitted by the irradiation unit 110.

When light is emitted from the direction of the arrow A, the light from the irradiation unit 110 passes through both the mechanical separator 320 and the serum 220 in the sample container 200, so that received amounts of transmitted light measured by the light receiving unit 120 gradually changes in a vertical direction of the mechanical separator 320. That is, since the change in the amount of received light is small, it is difficult to detect the interface. On the other hand, when light is emitted from the direction of the arrow B, the light receiving unit 120 alternately receives transmitted light only passing through the mechanical separator 320 and transmitted light only passing through the serum 220. Therefore, when the light is emitted from the direction of the arrow B, the change in the received amount of the transmitted light becomes large, so that the interface can be easily detected.

Therefore, in the present embodiment, in the measurement of transmitted light (step 403), the liquid level is detected more accurately by rotating the sample container 200 and detecting the transmitted light from a plurality of directions with respect to the sample container 200. FIG. 6 is a diagram showing a state in which the sample container 200 is irradiated with light from a plurality of directions to perform the measurement. The light is emitted so as to pass through a center axis of the sample container 200 even when the irradiation position is changed (that is, even when the sample container 200 rotates).

Subsequently, a flowchart of FIG. 7 shows a flow of analyzing the interface based on the data of the transmitted light acquired from the flowchart of FIG. 3.

A type of the separator 300 (step 800) is determined. The type of the separator 300 may be determined based on the data acquired in the flowchart of FIG. 3, and also be determined by acquiring information of the separator 300 from information (label, and the like) associated with the sample container 200. In a case where the separator 300 is the mechanical separator 320, a calculation method of an interface different from cases other than this case is used. When the separator 300 is identified as the gel 310, the beads 330, or is identified as no separator, which are not the mechanical separator 320, the processing proceeds to step 801.

The position of the interface is acquired based on the change in the amount of the transmitted light in data acquired by the measurement performed in the plurality of directions (step 801). FIG. 8A shows measurement when an upper end surface of the gel 310 is not horizontal. A highest position on the upper end surface of the gel 310 is a highest point 311, and a lowest position is a lowest point 312. FIG. 8B shows a state of measurement in which the sample container 200 of FIG. 8A is rotated 90 degrees clockwise when viewed from above. FIG. 8C shows data near the upper end surface of the gel 310 when the sample container 200 is irradiated with light that easily passes through the gel 310 and hardly passes through the serum 220. A vertical axis 901 of FIG. 8C indicates amounts of light received by the light receiving unit 120, and a horizontal axis 902 indicates positions (the position in the vertical direction of the sample container 200) of the irradiation position 502 on the irradiation path 501. Data 903 (dashed line) shows data measured in the state of FIG. 8A, and data 904 (solid line) shows data measured in the state of FIG. 8B. The amounts of received light of each data are compared from a left side to a right side (in the present embodiment, it means "from a lower side to an upper side of the sample container 200") of the horizontal axis 902 in FIG. 8C, so that a lowest point at which a change in the amount of received light starts is set to the lowest point 312, and a highest point at which the change in the amount of received light ends is set as the highest point 311.

In step 801, the highest points 311 and the lowest points 312 in each measurement direction are compared with each other, then the highest point 311 which is a highest position in the vertical direction of the sample container 200 is extracted as a highest position, and the lowest point 312 which is a lowest position is extracted as a lowest position (step 802).

In addition, an average point of the interface of the gel 310 is calculated (step 803). The average point means a position when the interface (upper end surface in the present embodiment) is horizontal without changing a volume of the gel 310. In a case of being irradiated with the light that easily passes through the gel 310 and hardly passes through the serum 220, at the positions irradiated with the light, when an amount of the gel 310 in the sample container 200 is large, the amount of the received light is small, and when the amount of the gel 310 is small, the amount of the received light is large. By calculating a sum of the amount of the received light from the lowest point 312 to the highest point 311, a ratio of the gel 310 existing from the lowest point 312 to the highest point 311 in the sample container 200 can be acquired, so that the average point of the upper end surface is calculated based on the ratio.

In the above description, the case where the gel 310 is used is described, but when the gel 310 is read as the clot 210, the interface can be detected as a case in which the separator 300 is not used. Further, in the above description, as the light from the irradiation unit 110, the light that easily passes through the gel 310 and hardly passes through the serum 220 is used, but light that hardly passes through the gel 310 and easily passes through the serum 220 may be used, and in this case, the amount of received light in FIG. 8C being large or small is reversed.

When it is determined in step 800 that the separator 300 is the mechanical separator 320, the processing proceeds to step 804. FIG. 9A shows a state of measuring the sample container 200 using the mechanical separator 320. FIG. 9B shows a state of measurement in which the sample container 200 of FIG. 9A is rotated 90 degrees clockwise when viewed from above. FIG. 9C shows data near an upper end surface of the mechanical separator 320 when the sample container 200 is irradiated with light that easily passes through the mechanical separator 320 and hardly passes through the serum 220. Data 905 (dashed line) in FIG. 9C shows data measured in the state of FIG. 9A, and data 906 (solid line) shows data measured in the state of FIG. 9B. In the data 905, the change in the amount of received light is small, and it is difficult to distinguish the change from noise. On the other hand, in the data 906 having a light irradiation angle different from that of the data 905, the change in the amount of received light is large, and can be easily distinguished from the noise. The amounts of received light of each data acquired by the measurement performed in a plurality of directions are compared, and a position in the vertical direction of the sample container 200 having a largest received amount is set as a peculiar point 907 (step 804).

Subsequently, a highest height at which the change in the amount of received light ends on the right side (in the present embodiment, it means "upper side of sample container 200") of the horizontal axis 902 from the peculiar point 907 is set to a height 321 of the upper end surface of the mechanical separator 320 (step 805). Similarly, a lowest height at which the change in the amount of received light ends on the left side (in the present embodiment, it means "lower side of sample container 200") of the horizontal axis 902 from the peculiar point 907 can be set to a height 322 of a lower end surface of the mechanical separator 320.

Even when the mechanical separator 320 is used as the separator 300, an interface other than the interface of the mechanical separator 320 can be acquired by a same procedure as in step 801 to step 803. At this time, the interface may be acquired only by step 801 and step 802, and step 803 is omitted.

Further, in the above description, interface positions of all the interfaces are acquired, and only the required interface position may be acquired. Further, the highest position, the lowest position, and the average position are acquired based on the data acquired in step 801, but only the necessary ones may be acquired. For example, when it is desired to acquire a probe lowering amount during sample dispensing, it is sufficient to acquire only the highest position of the interface between the separator 300 and the serum 220.

In this way, an algorithm is switched for each separator to detect the interface position. The gel 310 and the beads 330 are given as examples of the separator 300, but all separators having a shape or material that makes the transmitted light not different greatly depending on an angle at which the light is incident are targeted. Further, as another example, the mechanical separator 320 is mentioned, but all separators having a shape or material that makes the transmitted light different greatly depending on the angle at which the light is incident are targeted.

By performing measurement in a plurality of directions, a position of an end surface of a layer in the sample container 200 in which the sample having one or more layers is stored can be accurately detected. Further, by switching the algorithm that specifies the position of the end surface according to the type of separator 300 used in the sample container 200, an exact position of the end surface can be detected even when a separator having a shape other than that of the general gel 310 is used.

By calculating the highest position, the lowest position, and the average point of the interface based on the data acquired by the measurement performed in the plurality of directions, a liquid volume in each layer in the sample container 200 can be accurately estimated.

Second Embodiment

FIG. 10 is an overall configuration diagram of a liquid level detection device 100 according to another embodiment.

In the present embodiment, the sample container 200 gripped by the gripping portion 140 is not moved, but the irradiation unit 110 and the light receiving unit 120 are moved as a set. Therefore, instead of the first drive unit 150 and the second drive unit 160 of the first embodiment, the liquid level detection device 100 of the present embodiment includes a first drive unit 151 and a second drive unit 161 that move the irradiation unit 110 and the light receiving unit 120.

The first drive unit 151 moves the irradiation unit 110 and the light receiving unit 120 in the vertical direction of the sample container 200. The second drive unit 161 rotates the irradiation unit 110 and the light receiving unit 120 about the vertical direction of the sample container 200 as a rotation axis (that is, in the circumferential direction of the sample container 200).

FIG. 11 is a flowchart showing a flow of liquid level detection in the present embodiment. Only the operations that are changed from the operations in the first embodiment will be described.

The first drive unit 151 moves the irradiation unit 110 and the light receiving unit 120 to the measurement start position (step 1100). Positions of the irradiation unit 110 and the light receiving unit 120 at a start of measurement may be either above or below the sample container 200.

The sample container 200 is fixed at a measurement position, while the first drive unit 151 moves the irradiation unit 110 and the light receiving unit 120 in the vertical direction, and the light receiving unit 120 receives light that is emitted by the irradiation unit 110 and passes through the sample container 200, so that a received amount of transmitted light is measured (step 1101).

When a predetermined number of times of the measurement is not reached (1102), the second drive unit 161 rotates the irradiation unit 110 and the light receiving unit 120 to change a light irradiation direction (irradiation angle) with respect to the sample container 200 (step 1103), and returns to step 1100.

When the measurement is performed while moving the sample container 200 as in the first embodiment, an end surface of a layer may shake and noise may be included in a measured value. Since the sample container 200 is fixed in the present embodiment, the end surface of the layer can be prevented from shaking.

In each of the above-described embodiments, there is only one set of the irradiation unit 110 and the light receiving unit 120, but a plurality of sets of the irradiation unit 110 and the light receiving unit 120 may be provided in the horizontal direction. In this case, it is possible to shorten a time spent on the rotation operation for changing an angle at which the sample container 200 is irradiated with light. Further, a plurality of sets of the irradiation unit 110 and the light receiving unit 120 may be provided in the vertical direction. In this case, it is possible to shorten a time spent on the movement in the vertical direction.

The liquid level detection device according to each of the above-described embodiments is implemented as, for example, a stand-alone device, an automatic analysis device, a sample pretreatment device that automatically performs sample pretreatment, or as a part of a sample inspection automation system.

An example in which the liquid level detection device is implemented as a part of a sample inspection automation system will be described with reference to FIG. 12. FIG. 12 is a diagram showing an overall configuration of a sample inspection automation system.

The sample inspection automation system includes a pretreatment device 1200 that performs various pretreatments on a sample contained in the sample container 200, a plurality of analysis devices 1201 that perform analysis processing on the sample in the sample container 200 that is subjected to the pretreatment, a transport path 1202 that transports a holder 250 on which the sample container 200 is mounted between the pretreatment device 1200 and the analysis device 1201, a plurality of sample transfer units 1203 that are provided between the transport path 1202 and each of the plurality of analysis devices 1201 and transfer the sample container 200 between the holder 250 transported by the transport path 1202 and a rack used for mounting and transporting the sample container 200 on each analysis device 1201, and a control unit 1204 that controls operations of the entire sample processing system. The control unit 1204 includes an operation control unit that controls operations, and a storage unit that stores sample information such as analysis items and priority information of the sample contained in the sample container 200 loaded into the sample processing system, relationships between each identifier and the sample, and the like.

The pretreatment device 1200 is formed by connecting a plurality of units having various functions. The pretreatment device 1200 includes, for example, a sample loading unit 1200a, a sample containing unit 1200b, a centrifugation unit 1200c, a liquid volume measurement processing unit 1200d, an opening processing unit 1200e, a sub-sample container generation processing unit 1200f, a dispensing processing unit 1200g, and a closing processing unit 1200h.

The sample loading unit 1200a is a unit for loading the sample container 200 containing the sample into the sample inspection automation system. In addition, a sample recognition unit, a plug detection unit, and a sample holder recognition unit (not shown) are provided in the sample loading unit 1200a, a container type of the sample container 200 to be transported, a shape of a plug of the container, and ID information given to the holder 250 on which the sample container 200 is erected are recognized, so that information that identifies the sample container 200 to be transported is acquired. The sample holder recognition unit (not shown) is provided in various places in the sample inspection automation system, so that a location of the sample container 200 can be confirmed by the sample holder recognition unit at each place.

The centrifugation unit 1200c is a unit for centrifuging the loaded sample container 200.

The liquid volume measurement processing unit 1200d is a unit for measuring and discriminating an amount and a color of the sample loaded in the transported sample container 200 by a laser light source unit or an image recognition unit (not shown).

The opening processing unit 1200e is a unit for opening a plug (not shown) from the loaded sample container 200.

The sub-sample container generation processing unit 1200f is a unit for preparing another sample container 200 necessary for dispensing the sample contained in the loaded sample container 200 by the next dispensing processing unit 1200g, and attaching a barcode or the like.

The dispensing processing unit 1200g is a unit for subdividing the sample into another sample container 200 prepared by the sub-sample container generation processing unit 1200f, so that a sample that is not centrifuged or centrifuged by the centrifugation unit 1200c is analyzed by the analysis device 1201 or the like.

The closing processing unit 1200h is a unit for closing the plug in the sample container 200 in which the plug is opened or in the subdivided sample container 200. The sample inspection automation system may be provided with two or more closing processing unit 1200h, depending on a type of plug used for closing the sample container 200.

The sample containing unit 1200b is a unit for containing the sample container 200 closed by the closing processing unit 1200h.

This configuration is only an example, and other functional units may be provided in the pretreatment system. The units of the pretreatment device 1200 is connected by the transport path 1202, and the sample container 200 mounted on the holder 250 is transported by the transport path 1202.

The transport path 1202 is a mechanism that transports the sample container 200 loaded from the sample loading unit 1200a and the subdivided sample container 200 dispensed in the dispensing processing unit 1200g to each unit in the sample inspection automation system such as the centrifugation unit 1200c, the dispensing processing unit 1200g, and the analysis device 1201. The transport path 1202 is also used for transporting the sample container 200 to each mechanism unit that performs a predetermined operation in each unit such as the centrifugation unit 1200c, the dispensing processing unit 1200g, and the analysis device 1201.

The control unit 1204 controls the operations of each unit in the sample inspection automation system and each mechanism in each unit, and analyzes measurement data in the analysis device 1201. The control unit 1204 can communicate with each of the above-mentioned units and each mechanism, and can confirm the location of the sample in the sample inspection automation system based on the ID information of the holder 250.

The analysis device 1201 is a unit for performing qualitative and quantitative analysis of components on the transferred sample. As the analysis device 1201, various automatic analysis devices that analyze components of the pretreated sample, such as a biochemical analysis device, an immunity analysis device, and a coagulation analysis device, can be used depending on applications.

The liquid level inspection device 100 according to the above-described embodiment can be incorporated into, for example, the liquid volume measurement processing unit 1200d.

The invention is not limited to the above embodiment, and includes various modifications. For example, the embodiments described above have been described in detail for easy understanding of the invention, and are not necessarily limited to those including all the configurations described above. A part of the configuration of one embodiment can be replaced with the configuration of another embodiment, and the configuration of another embodiment can be added to the configuration of one embodiment.

REFERENCE SIGN LIST

100 liquid level detection device
110 irradiation unit
120 light receiving unit
130 analysis unit
140 gripping portion
150 first drive unit
151 first drive unit
160 second drive unit
161 second drive unit
170 control unit
200 sample container
210 clot
220 serum
250 holder
300 separator
310 gel
311 highest point
312 lowest point
320 mechanical separator
321 height of upper end surface
322 height of lower end surface
323 lower portion
330 beads
501 irradiation path
502 irradiation position

The invention claimed is:

1. A liquid level detection device comprising:
an irradiation unit configured to irradiate a side surface of a sample container containing a sample having layers with light;
a light receiving unit configured to receive transmitted light that is the light emitted from the irradiation unit and passing through the sample container;
an analysis unit configured to acquire an interface between the layers of the sample contained in the sample container based on received amounts of the transmitted light received by the light receiving unit;
a first drive unit configured to move the sample container in a vertical direction relative to the irradiation unit and the light receiving unit;
a second drive unit configured to move the sample container in a circumferential direction of the sample container relative to the irradiation unit and the light receiving unit; and
a control unit configured to control the first drive unit and the second drive unit,
wherein the control unit controls the second drive unit, so that the irradiation unit irradiates the sample container with the light at a first irradiation angle and a second irradiation angle different from the first irradiation angle, and the light receiving unit receives transmitted light that is the light passing through the sample container,
wherein the analysis unit acquires an interface between the layers of the sample based on received amounts of transmitted light at the first irradiation angle and the second irradiation angle by using an analysis method selected based on at least one of a type of a separator forming a layer in the container or presence or absence of the separator, wherein the separator includes a first separator having a small change in received amounts of transmitted light at the first irradiation angle and the second irradiation angle, and a second separator having a large change in received amounts of transmitted light at the first irradiation angle and the second irradiation angle, wherein when the separator is the first separator, the analysis unit acquires the interfaces at the first irradiation angle and the second irradiation angle based on a change in received amounts of the transmitted light in the vertical direction at the first irradiation angle and the second irradiation angle, compares the acquired interfaces at the first irradiation angle and the second irradiation angle, and acquires a highest position or a lowest position of the interface, and wherein when the separator is the second separator, the analysis unit compares changes in received amounts of the transmitted light in the vertical direction at the first irradiation angle and the second irradiation angle, and acquires the interface based on measurement data with a largest change in the received amounts of the transmitted light.

2. The liquid level detection device according to claim 1, wherein the second drive unit rotates a sample container.

3. The liquid level detection device according to claim 1, wherein the first drive unit moves the irradiation unit in a vertical direction of a sample container.

4. The liquid level detection device according to claim 1, wherein the second drive unit rotates the irradiation unit.

5. The liquid level detection device according to claim 1, wherein the first separator is at least one of a gel or beads, and the second separator is a mechanical separator.

6. The liquid level detection device according to claim 1, wherein the control unit controls the first drive unit, so that the irradiation unit irradiates the sample container in a vertical direction with the light at the first irradiation angle and the second irradiation angle, and the light receiving unit receives transmitted light that is the light passing through the sample container, and wherein the analysis unit acquires an interface between the layers of the sample based on a change in received amounts of the transmitted light in the vertical direction at the first irradiation angle and the second irradiation angle.

7. The liquid level detection device according to claim 6, wherein the analysis unit acquires the interfaces at the first irradiation angle and the second irradiation angle based on a change in received amounts of the transmitted light in the vertical direction at the first irradiation angle and the second irradiation angle, and acquires an average point of the acquired interfaces at the first irradiation angle and the second irradiation angle.

8. The liquid level detection device according to claim 7, wherein the analysis unit acquires an average position of the interface by using a ratio of received amounts of transmitted light based on a sum of the received amounts of the transmitted light from the lowest position to the highest position of the interface.

* * * * *